United States Patent [19]

Baker et al.

[11] Patent Number: 5,384,408
[45] Date of Patent: Jan. 24, 1995

[54] SUBSTITUTED PYRAZINE AND ITS SALTS, COMPOSITIONS CONTAINING THEM AND THEIR USE IN MEDICINE

[75] Inventors: Raymond Baker, Much Hadham, England; Victor J. Lotti, Harleysville, Pa.; Graham A. Showell, Welwyn Garden City, England

[73] Assignee: Merck Sharpe & Dohme Ltd., Hoddesdon, United Kingdom

[21] Appl. No.: 28,853

[22] Filed: Mar. 10, 1993

Related U.S. Application Data

[63] Continuation-in-part of Ser. No. 748,612, Aug. 22, 1991, abandoned.

[51] Int. Cl.$^6$ .................. C07D 453/02; A61K 31/495
[52] U.S. Cl. .................................. 544/336; 544/409; 546/137
[58] Field of Search .................. 544/336; 514/254

[56] References Cited

U.S. PATENT DOCUMENTS 5,073,557 12/1991 Baker et al. .................. 544/336

FOREIGN PATENT DOCUMENTS 239309 of 0000 European Pat. Off. .
327155 1/1989 European Pat. Off. .

OTHER PUBLICATIONS

*Basic and Clinical Pharmacology* by Bertram G. Katzung, (4th. Ed.) (1989), pp. 70–71, 78–79.
Drugs and Ther. Bulletin (Commerce Association of Britain) 1989, vol. 21, p. 85.
Heel et al Drugs, 1979, vol. 17, 38.
Br. J. Pharmac., vol. 92, pp. 817–826 (1987), by Newberry, et al.
Br. J. Pharmac., vol. 101, pp. 575–580 (1990), by Freedman, et al.
The New England Journal of Medicine, Oct. 12, 1989, pp. 1022–1029—"Muscarinic Receptor Subtypes" by R. K. Goyal.
J. of Ocular Pharmacology, (1990) vol. 6, No. 1, pp. 1–7, "Prostagandins Mediate . . . " by V. J. Lotti et al.
Br. J. Pharmacol. (1992) 107, 494–501, "L-689,660, a novel cholinominetic . . . " by R. J. Hargreaves et al.
"Glaxo Guide to Pharmacology" Mar. 1993, pp. 8, 14, published by Pharmacology Division Staff, Glaxo Group Research Ltd.
Med. Chem. Res. (1993) 3: 171–177, "L-696,986: A Functionally selective . . . " by G. A. Showell et al.
J. Med. Chem. 1987 30, pp. 969–975 "Synthesis and Characterization . . . " by J. Saunders et al.

*Primary Examiner*—Emily Bernhardt
*Attorney, Agent, or Firm*—Robert J. North; Joseph F. DiPrima

[57] ABSTRACT

3(R)-[2-(6-trifluoromethylpyrazin)yl]-1-azabicyclo[2.2.2]octane and its salts, and pharmaceutical formulations thereof are useful in medicine. In particular, they are useful for the treatment of neurological and mental illnesses whose clinical manifestations are due to cholinergic deficiency, and for lowering intraocular pressure. The compound may be prepared by dehydroxylating or decarboxylating the corresponding 3-hydroxy- or carboxy-quinuclidine analogue.

2 Claims, No Drawings

SUBSTITUTED PYRAZINE AND ITS SALTS, COMPOSITIONS CONTAINING THEM AND THEIR USE IN MEDICINE

CROSS-REFERENCE TO RELATED APPLICATIONS

The instant case is a continuation-in-part application of U.S. Ser. No. 07/748,612, filed Aug. 22, 1991, now abandoned.

The present invention relates to a substituted pyrazine compound which stimulates central muscarinic acetylcholine receptors and therefore is useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette syndrome. Alzheimer's disease, the most common dementing illness, is a slowly progressive neurological disorder characterised by marked deficits in cognitive functions including memory, attention, language and visual perception capabilities.

In addition, the compound is useful in treating glaucoma. Glaucoma is an ocular disorder associated with elevated intraocular pressures which are too high for normal function and may result in irreversible loss of visual function. If untreated, glaucoma may eventually lead to blindness. Ocular hypertension, i.e. the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Topical administration to the eye of agents such as pilocarpine may be used in order to improve the outflow of aqueous humour and reduce the intraocular pressure (see Drugs, 1979, vol 17, 38 and Drugs and Ther. Bull., 1989, vol 21, 85), but these have associated side effects such as emesis and myosis.

We have now found the compound lowers the intraocular pressure without exhibiting side effects to the extent associated with hitherto-known drugs used against glaucoma which act through cholinergic mechanisms.

European Patent Application No. 89200147 (Publication No. 327155) discloses a class of pyrazines, pyridazines or pyrimidines, and salts and prodrugs thereof, substituted on one of the ring carbon atoms thereof with a non-aromatic azacyclic or azabicyclic ring system; and independently substituted on each of the other ring carbon atoms with a substituent of low lipophilicity or a hydrocarbon substituent, which compounds stimulate cholinergic transmission. It has now been found that a compound of this class behaves as a functionally selective muscarinic agonist. This results in the compound exhibiting $M_1$ partial agonist activity (as measured in the rat ganglion) but $M_2$ and $M_3$ antagonist activity (as measured in the guinea pig heart and guinea pig ileum, respectively). In addition, the compound of this class effects reduction of intraocular pressure without exhibiting severe adverse effects on pupil size.

Thus, the present invention provides 3R-[2-(6-trifluoromethylpyrazin)yl]-1-azabicyclo[2.2.2]octane and salts thereof (hereinafter collectively referred to as compound (I)).

Also included within the scope of the present invention are salts of 3R-[2-(6-trifluoromethyl-pyrazin)yl]-1-azabicyclo[2.2.2]octane. It will be appreciated that salts of the compound for use in medicine will be non-toxic pharmaceutically acceptable salts. Other salts may, however, be useful for the preparation of the base or its non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, oxalic acid, succinic acid, acetic acid, citric acid, tartaric acid, carbonic acid or phosphoric acid. Preferred is the hydrogen tartrate. It will be appreciated by the person skilled in the art that the salts of the compound vary in their optical rotation. For example, the hydrogen oxalate salt of the (+)-base is (−)-3-[2-(6-trifluoromethylpyrazin)yl]-1-azabicyclo-[2.2.2]octane hydrogen oxalate and the hydrogen tartrate salt of the (+)-base (−)-3-[2-(6-trifluoromethyl-pyrazin)yl]-1-azabicyclo[2.2.2]octane hydrogen tartrate.

This invention also provides a method of treating Alzheimer's disease, senile dementia of the Alzheimer type, Huntington's chorea, tardive dyskinesia, hyperkinesia, mania or Tourette syndrome by the administration to a patient in need of such treatment of a pharmacologically effective amount of compound (I).

It may, where appropriate, be advantageous, in order to reduce unwanted peripherally mediated side-effects, to incorporate into the composition a peripherally acting cholinergic antagonist (or antimuscarinic agent). Thus compound (I) may be administered together with a peripheral cholinergic antagonist such as N-methylscopolamine, N-methylatropine, propantheline, methantheline or glycopyrrolate.

It will be understood that any formulation may further comprise another active ingredient such as another antiglaucoma agent for example a topical carbonic anhydrase inhibitor.

Compound (I) can be administered orally, parenterally or rectally at a daily dose of about 0.001 to 10 mg/kg of body weight, preferably about 0.01 to 1 mg/kg, and may be administered on a regimen of 1–4 times a day. When a cholinergic antagonist is administered, it is incorporated at its conventional dose.

When administered for the treatment of elevated intraocular pressure or glaucoma, the active compound is preferably administered topically to the eye, although systemic treatment is, as indicated, also possible. The dose administered can be from as little as 0.1 to 25 mg or more per day, singly, or preferably on a 2 to 4 dose per day regimen although a single dose per day is satisfactory.

This invention also provides a pharmaceutical composition comprising compound (I) and a pharmaceutically acceptable carrier therefor. It further provides the use of compound (I) for the preparation of a medicament for the treatment of the illnesses mentioned hereinbefore.

When given systemically, the drug can be given by any route, although the oral route is preferred. In oral administration, the drug can be employed in any of the usual dosage forms such as tablets, pills, capsules, powders, granules, sterile parenteral solutions or suspensions, or suppositories which forms are for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of compound (I). When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, acetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinylpyrrolidone and gelatin.

When given by the topical route, the active compound or an ophthalmologically acceptable salt thereof such as the hydrochloride salt is formulated into an ophthalmic preparation. In such formulations, from 0.0005% to 15% by weight can be employed. The objective is to administer a dose of from 0.1 to 1.0 mg per eye per day to the patient, with treatment continuing so long as the condition persists.

Thus, in an ophthalmic solution, insert, ointment or suspension for topical delivery, or a tablet, intramuscular or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. A preferred composition is eye drops. Formulations of these compounds may contain from 0.0005 to 15% and especially 0.05% to 2% of medicament. Higher dosages as, for example, about 10% or lower dosages can be employed provided the dose is effective in reducing or controlling elevated intraocular pressure. As a unit dosage from between 0.001 to 10.0 mg, preferably 0.005 to 2.0.mg, and especially 0.1 to 1.0 mg of the compound is generically applied to the human eye, generally on a daily basis in single or divided doses so long as the condition being treated exists.

This invention therefore further provides a pharmaceutical formulation adapted for topical administration to the eye which formulation comprises a compound of formula (I) and a carrier suitable for topical administration.

These hereinbefore described dosage values are believed accurate for human patients and are based on the known and presently understood pharmacology of the compounds, and the action of other similar entities in the human eye. As with all medications, dosage requirements are variable and must be individualized on the basis of the disease and the response of the patient.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical formulation may also be in the form of a solid insert such as one which after dispensing the drug remains essentially intact, or a bioerodible insert that is soluble in lacrimal fluids or otherwise disintegrates.

The present invention therefore further provides a process for preparing a pharmaceutical composition according to the invention which process comprises bringing compound (I) into association with a carrier therefor, such as by mixing.

Compound (I) may be prepared by a process which comprises the dehydroxylation or decarboxylation of a compound of formula (III) or a salt thereof:

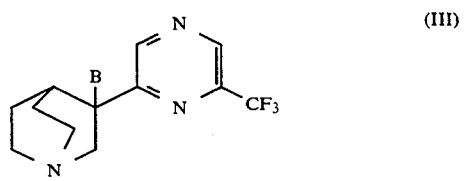
(III)

wherein B represents hydroxy or a carboxy-containing group such as the residue of a carboxylic acid or ester thereof. Preferably, B is —OH.

When the group B in compound (III) is hydroxy, it may be removed by chlorination and elimination, followed by hydrogenation. For example, chlorination and elimination may be effected by treatment with phosphorus oxychloride in the presence of triethylamine, or with thionyl chloride followed, where necessary, by DBN. The chloride or the unsaturated product may then be hydrogenated under conventional conditions, such as over 10% palladium/carbon in methanol. Alternatively, the compound (III) may be dehydroxylated by the use of thionyl chloride followed by treatment with tributyl tin hydride in a solvent such as tetrahydrofuran in the presence of a radical initiator such as azabisisobutyronitrile.

The compound of formula (III) where B is hydroxy may be prepared by reaction of a ketone compound of formula (IV) with a metal derivative of 2-trifluoromethylpyrazine, of formula (V):

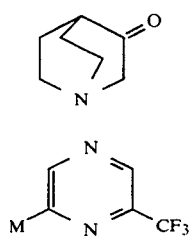

wherein M represents a metal atom, for example lithium. The lithium derivative for instance may be prepared by reacting the corresponding iodo-substituted pyrazine (V) with t-butyl lithium.

When the group B in compound (III) is carboxy it may be removed by standard decarboxylation techniques such as heating in aqueous solution made to pH1 with hydrochloric acid.

The compounds of formula (III) where B represents a carboxy-containing group may be prepared by reaction of a compound of formula (VI) with a compound of formula (VII):

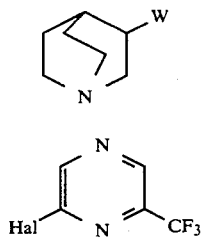

wherein Hal represents halo such as iodo, chloro or bromo; and W represents cyano, or a carboxylic acid group or a derivative thereof which activates the adjacent position, such as an alkyl ester; and subsequently, where necessary, converting the group W to a carboxy-containing group, preferably by hydrolysis.

Preferably, W represents an alkyl ester group such as methoxycarbonyl. Preferably, the halo group is chloro. The reaction between compounds (VI) and (VII) may be carried out in the presence of a strong base such as lithium diisopropylamide (which may be prepared in situ from n-butyl lithium and diisopropylamine) in a solvent such as tetrahydrofuran.

The 1-azabicyclo[2.2.2]octane moiety may be introduced into the molecules concerned by methods known from the art, in particular by methods analogous to those described in EP-A-0239309.

The separation of the enantiomers of the racemate corresponding to the compound (I) is preferably undertaken by optical resolution using (+)-di-O,O'p-toluyl-D-tartaric acid. The present invention therefore further provides a method for resolving the enantiomers of 3-[2-(6-trifluoromethylpyrazin)yl]-1-azabicyclo[2.2.2]octane using a chiral acid resolution.

The following Examples illustrate the preparation and use of compound (I). In the Examples, all temperatures are in °C.; THF is tetrahydrofuran; and ether is diethyl ether.

EXAMPLE 1

(R)-(+)-3-[2-(6-Trifluoromethylpyrazin)yl]-1-azabicyclo[2.2.2]octane (a) 2-Iodo-6-trifluoromethylpyrazine A three liter flask was charged with a solution of 2-amino-6-trifluoromethylpyrazine (obtained by the method of J. L. Miesel, U.S. Pat. No. 4,293,552, 95% pure by HPLC analysis, 32.6 g, 0.20 mol) in chloroform (1000 mL). Freshly ground iodine (101 g. 0.40 mol) was added to give a dark purple solution. After 40 min, a solution of t-butyl nitrite (22.9 g, 0.20 mol) in chloroform (300 mL) was added dropwise over 1 h. During the addition, slow gas evolution was observed together with a mild exotherm (<10° C.) which was moderated with a cold water bath. After an additional 1 h at room temperature the reaction mixture was washed with saturated aqueous sodium sulfite (3×500 mL) to remove the excess iodine. The chloroform solution was dried over magnesium sulphate, filtered and concentrated on a Buchi to give 23 g of an orange oil. The crude product was purified by distillation from copper (40–80 mesh, 200 mg) to give 19.5 g of the title compound as a yellow oil; b.p. 50°–56° C./0.6 mmHg; δ (360 MHz, CDCl$_3$) 9.06 (1H, s, pyrazine-H), 8.86 (1H, s, pyrazine-H); m/e 274 (M+).

(b) 3-Hydroxy-3-[2-(6-trifluoromethylpyrazin)yl]-1-azabicyclo[2.2.2]octane

A 500 mL flask was charged with 2-iodo-6-trifluoromethylpyrazine (prepared as in Example 1a, 5.0 g, 18.2 mmol) and ether (160 ml). The yellow solution was cooled to −110° C. with a liquid nitrogen/ether cooling bath. t-Butyl lithium (1.7M in pentane, 21.5 ml) was added dropwise over 15 min while maintaining the temperature below −100° C. The resulting muddy-brown mixture was stirred at −110° C. for 10 min. A solution of 3-quinuclidinone (2.28 g, 18.2 mmol) in ether (40 ml), which had been dried over molecular sieves (4 Å) for 1 h, was added dropwise over 10 min while maintaining the temperature below −100° C. The muddy-brown mixture was allowed to warm to −80° C. over 1 h before the reaction was quenched with methanol (3 ml). After warming to room temperature, water (200 ml) was added and the layers separated. The organic extract was washed with water (50 ml) and brine (50 ml), dried over magnesium sulphate, filtered and concentrated to a black oil. The crude product was purified by chromatography on 400 g of neutral alumina (grade III) using methanol/ethyl acetate (1:9) as eluent to give 1.57 g of the title compound as a brown solid. Recrystallisation from ether/hexane (1:1, 20 ml) gave 1.30 g of a tan powder; m.p. 118°–120° C.; Found: C, 52.76; H, 5.20; N, 15.22; F, 20.76 $C_{12}H_{14}F_3N_3O$ requires C, 52.74; H, 5.16; N, 15.38; F, 20.86; δ (360 MHz, CDCl$_3$) 9.16 (1H, s, pyrazine-H), 8.86 (1H, s, pyrazine-H), 3.88 (1H, dd, J=2.0, 14.4 Hz, H-2$_{ax}$), 3.05–2.75 (5H, m, H-2$_{eq}$, H2-6, H$_2$-7), 2.24 (1H, m, H-5), 2.02 (1H, m, H-4), 1.85 (1H, br, OH), 1.50 and 1.30 (3H, m, H-5, H$_2$-8); m/e 273 (M+).

(c)
3-Chloro-3-[2-(6-trifluoromethylpyrazin)yl]-1-azabicyclo[2.2.2]octane and (d)
3-[2-(6-trifluoromethylpyrazin)yl]-1-azabicyclo[2.2.2]oct-2-ene A solution of 3-hydroxy-3-[2-(6-trifluoromethylpyrazin)yl]-1-azabicyclo[2.2.]octane (prepared as in Example 1b, 4.45 g, 16.3mmol) in dichloromethane (45 ml) was cooled in an ice/water bath. Thionyl chloride (4.75 ml, 65.1 mmol) was added dropwise. The resulting black solution was heated at reflux for 90 min. After cooling to room temperature, the reaction mixture was concentrated to a black oil. The residue was cautiously dissolved in saturated aqueous sodium carbonate (100 ml) and the mixture extracted with ether (3×50 ml). The ethereal extract was washed with water (30 ml) and brine (30 ml), dried over magnesium sulphate, filtered and concentrated to a viscous black oil. Purification by chromatography on 400 g of neutral alumina (Grade III) using ethyl acetate/petrol (gradient of 1:4 to 2:3) as eluent gave first 1.83 g of 3-chloro-3-[2-(6-trifluoromethylpyrazin)yl]-1-azabicyclo[2.2.2]octane as a yellow solid; m.p. 53°–55° C.; δ (360 MHz, CDCl$_3$) 9.20 (1H, s, pyrazine-H), 8.86 (1H, s, pyrazine-H), 4.57 (1H, dd, J=2.2, 15.1 Hz, H-2ax), 3.38 (1H, d, J=15.1Hz, H-2$_{eq}$), 3.17–2.70 (4H, m, H$_2$-6, H$_2$-7), 2.56 (1H, m, H-4), 2.40 (1H, m, H-5), 1.65 and 1.12 (3H, m, H-5 and H$_2$-8); m/e 291 (M+). Hydrogen oxalate salt; m.p. 168°–170° C. (isopropanol); Found: C, 44.15; H, 3.92; N, 10.83; Cl, 9.53; F, 14.99. $C_{14}H_{15}N_3ClF_3O_4$ requires C, 44.05; H, 3.96; N, 11.01; Cl, 9.29; F, 14.93. Second to elute was 1.42 g of 3-[2-(6-trifluoromethylpyrazin)yl]-1-azabicyclo[2.2.2]oct-2-ene as a tan solid; m.p. 50°–54° C.; δ (360 MHz, CDCl$_3$) 8.98 (1H, s, pyrazine-H), 8.75 (1H, s, pyrazine-H), 7.43 (1H, s, H-2), 3.64 (1H, s, H-4), 3.07 (2H, m, H$_2$-6), 2.67 (2H, m, H$_2$-7), 1.86–1.50 (4H, m, H$_2$-5, H$_2$-8); m/e 255 (M+). Hydrogen oxalate salt; m.p. 205°–207° C. (ethanol); Found: C, 48.72; H, 3.94; N, 12.15; F, 16.79. $C_{14}H_{14}N_3F_3O_4$ requires C, 48.70; H, 4.09; N, 12.17; F, 16.51.

(e)
(±)-3-[2-(6-Trifluoromethylpyrazin)yl]-1-azabicyclo[2.2.2]octane

Method A

A slurry of 10% palladium on charcoal (20 mg) in methanol (5 ml) was added to a solution of 3-chloro-3-[2-(6trifluoromethylpyrazin)yl]-1-azabicyclo[2.2.2]octane (prepared as in Example 1c, 1.58 g, 5.42 mmol) and sodium acetate (0.44 g, 5.42 mmol) in methanol (35 ml). The resulting suspension was hydrogenated in a Parr apparatus at 50 psi for 1 h. The mixture was filtered to remove the catalyst and concentrated on a Buchi. The residue was dissolved in saturated aqueous sodium carbonate (40 ml) and extracted with ether (3×25 ml). The ethereal extract was washed with water (10 ml) and brine (5 ml), dried over magnesium sulphate and concentrated to a dark orange oil. The crude product was purified by chromatography on 180 g of neutral alumina (grade III) using methanol/ethyl acetate (1:9) as eluent to give 1.24 g of the title compound as a yellow oil. On standing at −20° C. for 1 day the product solidified; m.p. 27°–30° C. A portion of the product was distilled by Kugelrohr; b.p. 180°–190° C. (bath)/0.5 mmHg; Found: C, 55.30; H, 5.76; N, 16.20; F, 22.08. $C_{12}H_{14}N_3F_3$ requires C, 56.03; H, 5.49; N, 16.33; F, 22.15; δ (360 MHz, CDCl$_3$) 8.78 (1H, s, pyrazine-H), 8.68 (1H, s, pyrazine-H), 3.56–2.80 (7H, m, H$_2$-2, H-3, H$_2$-6 and H$_2$-7), 2.05 (1H, m, H-4), 1.84–1.28 (4H, m, H$_2$-5 and H$_2$-8); m/e 257 (M+). Hydrogen oxalate salt hemihydrate; m.p. 109°–111° C. (isopropanol); Found: C, 47.44; H, 4.61; N, 11.68. $C_{14}H_{16}N_3F_3.0.5H_2O$ requires C, 47.19; H, 4.81; N, 11.79.

Method B

A slurry of 10% palladium on charcoal (80 mg) in methanol (5 ml) was added to a solution of 3-[2-(6trifluoromethylpyrazin)yl]-1-azabicyclo[2.2.2]oct-2-ene (prepared as in Example 1d, 1.19 g, 4.66 mmol) and sodium acetate (0.38 g, 4.66 mmol) in methanol (35 ml). The resulting suspension was hydrogenated in a Parr apparatus at 50 psi for 2 h. The mixture was filtered to remove the catalyst before a slurry of fresh 10% palladium on charcoal (80 mg) in methanol (5 ml) was added. The resulting suspension was hydrogenated in a Parr apparatus at 50 psi for 2 h. The mixture was filtered to remove the catalyst and concentrated on a Buchi. The residue was dissolved in saturated aqueous sodium carbonate (40 ml) and extracted with ether (3×25 ml). The ethereal extract was washed with water (10 ml) and brine (5 ml), dried over magnesium sulphate and concentrated to an orange oil. The crude product was purified by chromatography on 180 g of neutral alumina (grade III) using methanol/ethyl acetate (gradient of 1:19 to 1:9) as eluent to give first 0.11 g of recovered starting material followed by 0.91 g of the title compound as a yellow oil; analytical data as described in Method A.

(f)
(R)-(+)-3-[2-(6-Trifluoromethylpyrazin)yl]-1-azabicyclo[2.2.2]octane di-O,O′-p-toluyl-D-tartrate A solution of (+)-di-O,O′-p-toluyl-D-tartaric acid (1.21 g, 3.14 mmol) in ethanol (10 ml) was added to a solution of (±)-3-[2-(6-trifluoromethylpyrazin)yl]-1-azabicyclo[2.2.2]octane (prepared as in Example 1e, 3.23 g, 12.6 mmol) in ethanol (25 ml). After about 20 seconds a white precipitate formed. The resulting slurry was stirred at room temperature for 1 h. The solid was collected by filtration, washed with ethanol (10 ml) and air-dried for 1 h to give 2.4 g of a white powder. The mother liquors were placed to one side. The solid was triturated with ethanol (20 ml) at reflux for 1 h, filtered hot, washed with ethanol (5 ml) and air-dried for 1 h. The triturated procedure was repeated two additional times to give 1.4 g of the title compound as a white powder; m.p. 185°–6° C.; [α]$^{23}$+47° (c 0.71, methanol); 98% ee by HPLC (5 μm, AGP, 10 mM K$_2$HPO$_4$, pH 7.0); Found: C, 58.35; H, 5.26; N, 9.10; F, 12.67. $C_{44}H_{46}N_6F_6O_8$ requires C, 58.66; H, 5.15; N, 9.33; F, 12.65; δ (360 MHz, D$_2$O) 8.95 (1H, s, pyrazine-H), 8.89 (1H, s, pyrazine-H), 8.00 (2H, d, J=8.2 Hz, Ar-H), 7.37 (2H, d, J=8.2Hz, Ar-H), 5.67 (1H, s, CHCOOH), 4.09 (1H, dd, J=5.8, 12.8 Hz, H$_2$-ax), 3.87 (1H, m, H$_2$-eq), 3.66–3.26 (5H, m, H-3, H$_2$-6 and H$_2$-7), 2.46 (1H, m, H-4), 2.42 (3H, s, Ar-CH₃), 2.18 and 1.76 (4H, m, H₂-5 and H₂-8); m/e 257 (M+).

The mother liquors from the resolution (50% ee by HPLC) were racemised by the following procedure:

Ethanol was removed on a Buchi. The residue was dissolved in saturated aqueous sodium carbonate and extracted with ether (×3). The ethereal extract was washed with water and brine, dried over magnesium sulphate and concentrated to give 2.1 g of an orange oil. Sodium (0.7 g) was dissolved in isopropanol (100 ml) and the resulting solution added to the free base. The solution was stirred at room temperature for 15 h. Isopropanol was removed on a Buchi. The residue was dissolved in water (50 ml) and extracted with ether (×3). The ethereal extract was washed with water and brine, dried over magnesium sulphate and concentrated to an orange oil. Purification by chromatography on 300 g of neutral alumina (grade III) using methanol-/ethyl acetate (1:9) as eluent gave 1.82 g of (±)-3-[2-(6-trifluoromethylpyrazin)yl]-1-azabicyclo[2.2.2]octane as a yellow oil which was racemic by HPLC analysis.

(g)
(R)-(±)-3-[2-(6-Trifluoromethylpyrazin)yl]-1-azabicyclo[2.2.2]octane

Sodium carbonate (3.2 g) was added to a slurry of (+)-3-[-2-(6-trifluoromethylpyrazine)yl]-1-azabicyclo[2.2.2]octane di-O,O-p-toluyl-D-tartrate (prepared as in Example 1f, 5.65 g, 12.5 mmol) in water (50 ml) cooled in an ice/water bath. Ethyl acetate (50 ml) was added and the mixture stirred at 0° C. for 10 min, until the white solid had dissolved. The layers were separated and the aqueous re-extracted with ethyl acetate (2×25 ml). The combined organic extracts were dried over magnesium sulphate and concentrated. The residue was dissolved in ether (40 ml), filtered through a grade 4 scintered funnel, and concentrated to give 3.19 g of the title compound as a faint yellow oil. An analytical sample was obtained by Kugelrohr distillation; b.p. 140°-150° C. (bath)/0.2 mmHg; $[\alpha]^{23} +23°$ (c 0.88, methanol), +71° (c 0.89, acetonitrile), +73° (c 0.84; dichloromethane); 98% ee by HPLC (5 μm AGP, 10 mM K₂HPO₄, pH 7.0); Found: C, 55.63; H, 5.40; N, 16.05; F, 21.97. C₁₂H₁₄N₃F₃ requires C, 56.03; H, 5.49; N, 16.33; F, 22.15; δ (360 MHz, CDCl₃) 8.78 (1H, s, pyrazine-H), 8.68 (1H, s, pyrazine-H), 3.56–2.80 (7H, m, H₂-2, H-3, H₂-6 and H₂-7), 2.05 (1H, m, H-4), 1.84–1.28 (4H, m, H₂-5 and H₂-8); m/e 257 (M+).

EXAMPLE 2

(S)-(+)-3-[2-(6-Trifluoromethylpyrazin)yl]-1-azabicyclo[2.2.2]octane hydrogen oxalate A solution of (−)-di-O,O'-p-toluyl-L-tartaric acid hydrate (0.63 g, 1.56 mmol) in ethanol (10 ml) was added to a solution of (±)-3-[2-(6-trifluoromethyl-pyrazin)yl]-1-azabicyclo[2.2.2]octane (prepared as in Example 1e, 1.60 g, 6.24 mmol) in ethanol (15 ml). A white precipitate formed and the resulting slurry was stirred at room temperature for 1 h. The solid was collected by filtration and air-dried. The solid was triturated with ethanol (15 ml) at reflux for 1h, filtered and air-dried. The trituration procedure was repeated two additional times to give 0.90 g of (−)-3-[2-(6-trifluoromethylpyrazine)yl]-1-azabicyclo[2.2.2]octane di-O,O-p-toluyl-L-tartrate as a white powder. The solid was dissolved in saturated aqueous sodium carbonate (20 ml) and extracted with ethyl acetate (×3). The organic extract was dried over magnesium sulphate, filtered and concentrated. The free base was dissolved in ether (20 ml) and added to a solution of oxalic acid (0.20 g, 2.2 mmol) in ether (30 ml). The resulting solid was triturated with ether and recrystallised from a minimum volume of isopropanol to give 0.60 g of the title compound as a white powder; m.p. 170°–171° C.; [α] (22° C.,D)+14° (c 0.36, methanol); 98.6% ee by HPLC (5 μm AGP, 10 mM K₂HPO₄, pH 7.0); Found: C, 48.44; H, 4.67; N, 11.77. C₁₄H₁₆N₃F₃O₄ requires C, 48.42; H, 4.64; N, 12.10; δ (360 MHz, D₂O) 8.94 (1H, s, pyrazine-H), 8.88 (1H, s, pyrazine-H), 4.11 (1H, dd, J=6, 13Hz, H₂-ax), 3.89 (1H, m, H₂-eq), 3.72–3.28 (5H, m, H-3, H₂-6 and H₂-7), 2.47 (1H, m, H-4), 2.16 and 1.77 (4H, m, H₂-5 and H₂-8); m/e 257 (M+).

DESCRIPTIVE EXAMPLE 3

(R)-(−)-3-[-2-(6-Trifluoromethylpyrazin)yl]-1-azabicyclo[2.2.2]octane hydrogen oxalate A solution of (+)-3-[2-(6-trifluoromethylpyrazin)yl]-1-azabicyclo[2.2.2]octane (prepared as in Example 1g, 0.59 g, 2.3 mmol) in ether (20 ml) was added to a solution of oxalic acid (0.23 g, 2.5 mmol) in ether (30 ml). The resulting solid was triturated with ether and recrystallised from a minimum volume of isopropanol to give 0.72 g of the title compound as a white powder; m.p. 170°–172° C.; [α] (22° C.,D)−16° (c 0.35, methanol); 97.6% ee by HPLC (5 μm AGP, 10 mM K₂HPO₄, pH 7.0); Found: C, 48.30; H, 4.72; N, 11.98. C₁₄H₁₆N₃F₃O₄ requires C, 48.42; H, 4.64; N, 12.10; δ (360 MHz, D₂O) 8.94 (1H, s, pyrazine-H), 8.88 (1H, s, pyrazine-H), 4.11 (1H, rid, J=6, 13 Hz, H₂-ax), 3.89 (1H, m, H₂-eq), 3.72–3.28 (5H, m, H-3, H₂-6 and H₂-7), 2.47 (1H, m, H-4), 2.16 and 1.77 (4H, m, H₂-5 and H₂-8); m/e 257 (M+).

DESCRIPTIVE EXAMPLE 4

(R)-(−)-3-[2-(6-Trifluoromethylpyrazin)yl]-1-azabicyclo[2.2.2]octane hydrogen L-tartrate A solution of (+)-3-[2-(6-trifluoromethylpyrazin)yl]-1-azabicyclo[2.2.2]octane (prepared as in Example 1g, 3.02 g, 11.7 mmol) in ethanol (20 ml) was added to a solution of (+)-L-tartaric acid (1.94 g, 12.9 mmol) in ethanol (30 ml). After 2 d at room temperature the resulting white solid was collected by filtration, washed with ice-cold ethanol (20 ml) and air-dried. The solid was redissolved in hot ethanol (70 ml), filtered and allowed to cool to room temperature. After 12 h at +2° C. the resulting crystals were collected by filtration, washed with ice-cold ethanol (20 ml) and air-dried. After further drying at 60° C. under high vacuum 4.06 g of the title compound was obtained as white crystals; m.p. 166°–168° C.; [α] (23° C.,D)−1.7° (c 0.93, methanol); 98% ee by HPLC (5 μm AGP, 10 mM K₂HPO₄, pH 7.0); Found: C, 47.19; H, 4.99; N, 10.26; F, 13.92. C₁₆H₂₀N₃F₃O₆ requires C, 47.17; H, 4.95; N, 10.32; F, 13.99; δ (360 MHz, D₂O) 8.94 (1H, s, pyrazine-H), 8.89 (1H, s, pyrazine-H), 4.50 (2H, s, tartaric acid), 4.11 (1H, dd, J=6.0, 12.9Hz, H₂-ax), 3.89 (1H, m, H₂-eq), 3.72–3.28 (5H, m, H-3, H₂-6 and H₂-7), 2.47 (1H, m, H-4), 2.17 and 1.77 (4H, m, H₂-5 and H₂-8); m/e 257 (M+).

PHARMACEUTICAL EXAMPLES

| | Amount - mg |
|---|---|
| 1. Tablets containing 1-25 mg of compound (I) | |

-continued

|  | Amount - mg |  |  |
|---|---|---|---|
| Compound (I) | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| 2. Tablets containing 26-100 mg of compound (I) | | | |
| Compound (I) | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

Compound (I), lactose, and a portion of the corn starch are mixed together and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of compound (1) per tablet.

Eye Drops

| The pharmaceutically acceptable salt of the active compound | 0.5% |
|---|---|
| Benzalkonium chloride solution | 0.02% v/v |
| Disodium edetate | 0.05% |
| NaCl | 0.8% |
| Water for injections | to 100% |

The formulation is sterilised by autoclaving.

BIOLOGICAL DATA

1. By the methods disclosed in J. Med. Chem. (1987), 30, 969–975 was determined the functional selectivity of compound (I):

| Compound | Ganglion (EC$_{50}$ - μm) M$_1$ | Heart (pA$_2$) M$_2$ | Ileum (pA$_2$) M$_3$ |
|---|---|---|---|
| (I): (+) base isomer | 0.2 | [7.8] | [7.8] |
| Comparative data for corresponding | | | |
| (−) base isomer | no agonist effect | [7.0] | [7.2] |
| (±) racemate | 0.5 | [7.6] | [7.1] |

2. Glaucoma method

Male or female African Green monkeys (2.0–4.5 kg) were fasted following their afternoon feeding on the day prior to the experiment. The monkeys were anaesthetised in their cages with approximately 10 mg/kg i.m. ketamine HCl (Vetalar or Ketaset). Once sedated, the animals were restrained in monkey chairs and brought to the laboratory. One drop of 0.5% proparacaine (Ophthetic) was instilled into each eye. After 30 seconds, intraocular pressure (IOP) determinations were taken in each eye (control or "0" time reading) using a Digilab Modular One Pneuma Tonometer. Both eyes were then flushed with saline. Vehicle or test agent (0.0005–2.0%) was administered (25 μl) into the cul-de-sac of both eyes and the IOP was determined at 0.5 and 1.0 hour and at hourly intervals thereafter for up to 5 hours and compared to the control IOP. For ocular instillation, 0.5% hydroxyethylcellulose (HEC) was employed as the vehicle. Supplemental doses of 10 mg or more/animal i.m. ketamine HCl were given 3–5 minutes prior to IOP determinations. Proparacaine HCl (0.5%) (one drop/eye) was also instilled immediately prior to IOP determinations. Following the final IOP determination, both eyes were flushed liberally with saline and a sterile ophthalmic ointment (Ilotycin, erythromycin, 5 mg/gm) was applied. Animals were allowed to recover in their cages and a light meal was provided. At least 2 days separated individual intraocular pressure experiments. Pupil diameter was measured under standard laboratory lighting conditions using a millimeter ruler. ["Vetalar," "Ketaset", "Ophthetic"- 'Digilab Modular One" , and "Ilotycin" are all trade marks.]

| Compound | Concentration | Change in IOP[a] |
|---|---|---|
| (I): (+) base isomer | 0.05% | −3.5 |

FOOTNOTE:
[a]Maximum mm Hg change in intraocular pressure

3. M1 Muscarinic Activity

The following two compounds: 3(R)-[2-(6-trifluoromethyl) pyrazinyl]-1-azabicyclo[2.2.2]octane (Compound 1), and 3(R)-[2-(6chloro)pyrazinyl]-1-azabicyclo[2.2.2]octane (Compound 2) were tested for muscarinic activity using the method of Newberry, et al. (Br. J. Pharmacol, 1987, pp. 817–876). The specific M1 muscarinic activities of Compound 1 and Compound 2 were determined and the results are as follows:

Compound 1 EC$_{50}$ = 0.2 μM

Compound 2 EC$_{50}$ = 0.05 μM

Thus, both Compound 1 and Compound 2 were found to possess M1 muscarinic activity, and have utility in treating elevated intraocular pressure, and thereby treating or preventing associated ocular disorders such as glaucoma.

4. M3 Muscarinic Activity

Using the method described by Freedman, et al. (Br. J. Pharmacol, 1990, 101, pp. 575–580) involving ileum preparation, the M3 muscarinic activity of Compound 1 and Compound 2 were determined and the results were as follows:

Compound 1 pA$_2$ = 7.8

Compound 2 EC$_{50}$ = 0.03 μM

As is seen, the 6-CF$_3$ compound (Compound 1 ) has a positive pA$_2$ value of 7.8 in the ileum assay since it acts as antagonist on M3 receptors. There is no measurable pA$_2$ data for the 6-Cl compound (Compound 2) since it is an M3 receptor agonist.

By contrast, the 6-Cl compound exhibits an EC$_{50}$ value of 0.03 micromolar. The EC$_{50}$ is the excitatory concentration of test compound required to achieve 50% activation for the receptor under consideration. In this assay, only the agonist activity on the M3 receptor is measured. Thus, the 6-Cl compound yields a positive value while the 6-CF$_3$ compound does not since the 6-CF$_3$ compound is not an agonist at the M3 receptor.

It is clear from the above activity data for the 6-CF$_3$ compound, in comparison with the activity data for the 6-Cl compound of U.S. Pat. No. 5,073,557 to Baker, et al., that, while the 6-CF$_3$ compound retains M 1 muscarinic agonist activity comparable to that of the reference 6-Cl compound, the 6-CF$_3$ compound possesses significantly greater selectivity of action. The 6-Cl reference compound acts not only as an agonist on M1 receptors, but also undesirably acts as an agonist on M3 receptors. M3 receptor agonism is known to be associated with smooth-muscle contraction, which can lead to such undesirable effects as gastrointestinal distress and diarrhea. See *New England Journal of Medicine,* Vol. 321, No. 15, pp. 1022–1029 (1989), by Raj K. Goyal, and *TIPS,* December 1989 Supplement, pp. 85–88, by Julian A. Gray, et al. In contrast, the 6-CF$_3$ compound is not an agonist of M3 receptors, and thus would not cause stimulation of the M3 receptor leading to gastrointestinal distress.

Further, the African green monkey glaucoma test described above has predictive value for use in humans. See *J. Ocular Pharmacology,* Vol. 6, No. 1, 1990, pp. 1–7. by V. J. Lotti, et al.

Thus, the 6-CF$_3$ compound, which exhibits a positive lowering of intraocular pressure in the glaucoma test, exhibits the same effect in humans.

We claim:

1. A compound selected from 3(R)-[2-(6-trifluoromethylpyrazin)yl]-1-azabicyclo[2.2.2]octane or pharmaceutically acceptable salts thereof.

2. A compound according to claim 1 selected from 3(R)-[2-(6-trifluoromethylpyrazin)yl]-1-azabicyclo[2.2.2]octane hydrogen oxalate; and 3(R)-[2-(6-trifluoromethylpyrazin)yl]-1-azabicyclo[2.2.2]octane hydrogen tartrate.

* * * * *